United States Patent [19]

Ford

[11] Patent Number: 5,733,568
[45] Date of Patent: *Mar. 31, 1998

[54] MICRO-ENCAPSULATED LACTOBACILLI FOR MEDICAL APPLICATIONS

[75] Inventor: Larry C. Ford, Irvine, Calif.

[73] Assignee: Lafor Laboratories Limited, Newport Beach, Calif.

[ * ] Notice: The term of this patent shall not extend beyond the expiration date of Pat. No. 5,466,463.

[21] Appl. No.: 459,058

[22] Filed: Jun. 2, 1995

Related U.S. Application Data

[63] Continuation-in-part of Ser. No. 301,966, Sep. 7, 1994, Pat. No. 5,466,463, which is a continuation of Ser. No. 161,659, Dec. 3, 1993, abandoned.

[51] Int. Cl.$^6$ .............................. A61F 13/20; A61F 6/08; C12N 11/04; A61K 9/14
[52] U.S. Cl. .................................. 424/433; 424/DIG. 15; 424/489; 514/967
[58] Field of Search .......................... 424/433, DIG. 15, 424/489; 514/967; 435/853, 854

[56] References Cited

U.S. PATENT DOCUMENTS

| | | | |
|---|---|---|---|
| 4,579,734 | 4/1986 | Hata et al. | 424/93 |
| 4,983,163 | 1/1991 | Winans, Jr. et al. | 604/49 |
| 5,466,463 | 11/1995 | Ford | 424/433 |

FOREIGN PATENT DOCUMENTS 0047609  9/1976  Netherlands.

OTHER PUBLICATIONS

Monif, Gilles R.G. et al. "Quantitative and qulitative effects of povidone–iodine liquid and gel on the aerobic and anaerobic flora of the female genital tract", *Am. J. Obstet. Gynecol.* 137(4):432–438 (Jun. 15, 1980).

McGroarty, Jacqueline A. et al. "Development of Lactobacillus Probiotics", *Clinical Advances in the Treatment of Infections*, New York, pp. 16, 13–14.

McGroarty, Jacqueline A. and Moody, Karen J., "Nonoxynol–9 and Urogenital Infections in Women", *Clinical Advances in the Treatment of Infections*, p. 16, 12–14.

Sherris, Jacqueline D. et al. "New Developments in Vaginal Contraception", Population Reports, (By Population Information Program, The Johns Hopkins University), 12(1): H–159–191 (1984).

McGroarty, Jacqueline A. et al. "Influence of the spermicidal compound Nonoxynol–9 on the growth and Adhesion of Urogenital bacteria in vitro", *Current Microbiology*, vol. 21 (1990), 219–223.

McGroarty, Jacqueline A. et al. "Hydrogen Peroxide Production by Lactobaillus Species: Correlation with Susceptibility to the Spermicidal Compound Nonoxyno–9", *JID*, 1992:165(Jun.), 1142–1144.

McGroarty, J.A. et al. "Influence of the Spermicidal Compound Nonoxynol–9 on the Adhesion of *E coli* to Human Epithelial Cells", *Int Urogynecol J*, (1994)4: 194–198.

McGroarty, J.A. et al. "Modulation of Adhesion of Uropathogenic *Enterococcus faecalis* to Human Epithelia Cells in vitro by Lacto–bacillus species", *Microbial Ecology in Health and Disease*, vol. 5: 309–314 (1992).

McGroarty, Jacqueline A. et al. "The Spermicidal Compound Nonoxynol–9 Increases Adhesion of Candida Species to Human Epithelial Cells in Vitro", *Infection and Immunity*, 58(6): pp. 2005–2007, (Jun. 1990).

Kreiss, Joan et al. "Efficacy of Nonoxynol 9 Contraceptive Sponge Use in Preventing Heterosexual Acquisition of HIV in Nairobi Prostitutes", *JAMA*, Jul. 22/29, 1992, 268(4): 447–482.

Goldin, Barry R. and Gorbach, Sherwood L. "Alterations of the IntestinalMicroflora by Diet, Oral Antibiotics, and Lactobacillus: Decreased Production of Free Amines From Aromatic Nitro Compounds, Azo Dyes, and Glucuronides", *JNCI*, 73(3): 689–695(Sep. 1984).

Barefoot, Susan F. and Klaenhammer, Todd R. "Detection and Activity of Lactacin B, a Bacteriocin Produced by *Lactobacillus acidophilus*", *Applied and Environmental Microbiology*, 45(6):1808–1815(Jun., 1983).

Barefoot, Susan F. and Klaenhammer, Todd R. "Purification and Characterization of the *Lactobacillus acidophilus* Bacteriocin Lactacin B", *Antimicrobial Agents and Chemotherapy*, 26(3): pp. 328–334(Sep. 1984).

Mehta, A.M. et al. "Purification and properties of the inhibitory protein isolated from *Lactobacillus acidophilus* AC", *Microbios*, 38: pp. 73–81 (1983).

Silva, M. et al. "Antimicrobial Substance from a Human Lactobacillus Strain", *Antimicrobial Agents and Chemotherapy*, 31(8): pp. 1231–1233(Aug. 1987).

S. Leodolter, E. Reinold et al. "Ceftriaxon, I g i.v.–Effectively Prevents Infections and Is Cost Effective", *Program And Abstras—3rd World Congress for Infectious Diseases in Obstetrics and Gynecology combined with Infectious Diseases in Urology, Dermatology, and Clinical Immunology*, Acapulco, Mexico, 1993. p. 110.

Ford, L.C. et al. "In Vitro Antimicrobial Effects of the Inner Confidence Lactobacilli(*Lactobacillus Acidophilus* 6 *Lactobacillus Rhamnosus*)" *Program And Astrats—3rd World Congress for Infectious Diseases in Obstetrics and Gynecology combined with InfectiousDiseases in Urology, Dermatology and Clinical Immunology*, Acapulco, Mexico, 1993, p. 110.

Ford L.C. et al. "Safety of Inner Confidence Supportories", *Proram And Abstracts—3rd World Congress for Infectious Diseases in Obstetrics and Gynecology combined with Infectious Diseases in Urology, Dermatology and Clinical Immunology*, Acapulco, Mexico, 1993, p. 111.

Ford, L.C. et al. "Topical Therapy of Bacterial Vaginosis", *Program And Abstracts—1st World Congress for Infectious Diseases in Obstetrics and Gynecology*, Hawaii, USA, 1989, p. 78.

*Primary Examiner*—Carlos Azpuru
*Attorney, Agent, or Firm*—Klein & Szekeres, LLP

[57] ABSTRACT

Micro-encapsulated lactobacilli bacteria are orally administered to mammals, including humans, to treat or prevent antibiotic associated or other chronic or acute diarrhea. Micro-encapsulated lactobacilli bacteria are topically administered to the skin to treat or prevent recurrent skin infections, and are administered intra-vaginally to treat or prevent vaginal yeast infections.

5 Claims, No Drawings

MICRO-ENCAPSULATED LACTOBACILLI FOR MEDICAL APPLICATIONS

CROSS REFERENCE TO RELATED APPLICATION

The present application is a continuation-in-part of application Ser. No. 08/301,966 filed on Sep. 7, 1994, issued as U.S. Pat. No. 5,466,463, which is a continuation of application Ser. No. 08/161,659, filed on Dec. 3, 1993, now abandoned.

BACKGROUND OF THE INVENTION

1. Field of the Invention

The present invention is directed to a pharmaceutical composition in the form of capsules, tablets, creams, foams, ointments, powders, suppositories or the like containing micro-encapsulated lactobacilli for oral, topical and intravaginal administration for the treatment or prevention of antibiotic associated diarrhea, skin and vaginal infections.

2. Brief Description of the Prior Art

Antibiotic associated diarrhea is a common side effect of broad spectrum anti-bacterial therapy, and is believed to be due to a shift in intestinal flora as a result of therapy with antibiotics, and particularly due to loss of lactobacilli in the intestinal flora. This condition can become life-threatening to the patient and is very difficult to treat when it is caused by a *Clostridium difficile* bacterical infection.

It has been attempted in the prior art to treat antibiotic associated diarrhea with oral administration of lactobacilli. This type of therapy, however, has been proven to be of only limited success, for two primary reasons. First, orally administered lactobacilli, in accordance with the prior art, are exposed to the destructive action of gastric acid. Therefore only an inadequately small number of viable lactobacilli tend to reach the lower intestinal tract where they would be needed to reestablish a healthy lactobacilli flora. Second, transient lactose intolerance is frequently found in persons suffering from antibiotic associated diarrhea. (The temporary lactose intolerance is attributed by those skilled in the art to the loss of the brush border of the intestinal villa, caused by the antibiotic.) Moreover, this type of transient lactose intolerance frequently occurs even in persons who, otherwise under normal conditions, have no prior history of dairy product or lactose intolerance. Lactobacilli preparations in accordance with the prior art usually contain traces or remnants of the media in which the lactobacilli bacteria were grown and therefore contain lactose, lactulose and other disacharides. These in turn, upon reaching the lower intestines of persons suffering from antibiotic associated diarrhea, tend to make worse the transient lactose intolerance condition. In light of the foregoing, there is room for improvement in the prior art. More particularly, there is room in the prior art for improvement of pharmaceutical compositions and methods for the treatment of antibiotic associated diarrhea, and also for treatment or prevention of certain skin and vaginal infections. The present inventions provides such improvements.

SUMMARY OF THE INVENTION

In accordance with one aspect of the present invention more than approximately $10^3$ viable micro-encapsulated lactobacilli in each unit dose, are orally administered in a pharmaceutical composition or delivery vehicle, to persons suffering from antibiotic associated diarrhea. The lactobacilli are administered for the treatment or prevention of the diarrhea and this therapy is preferably continued during and shortly after treatment with the antibiotic. Administration of the micro-encapsulated lactobacilli may also be coupled with administration of metronidazole or other antibiotic which kill *Clostridium difficile* antibiotics. The micro-encapsulated lactobacilli survive in sufficient numbers the exposure to gastric acid while traveling through the stomach and reach the lower intestines where they help establish or reestablish a healthy bacterial flora, and eliminate or alleviate the symptoms of antibiotic associated diarrhea.

In another aspect of the present invention a pharmaceutical composition containing micro-encapsulated lactobacilli is applied topically to the skin to prevent or treat skin infections, or a vaginal cream, foam, ointment or suppository is used to prevent or treat vaginal infections.

A large variety of delivery vehicles, such as gelatin capsules, tablets or liquid dosage forms may be used for oral administration of the micro-encapsulated lactobacilli. Similarly, a large variety of delivery vehicles, such as creams, foams, ointments, suppositories, or admixtures with inert powders such as starch or talcum powder may be used for topical and/or vaginal administration, as applicable, of the micro-encapsulated lactobacilli.

The following is a detailed description of the invention, and a summary of certain tests and results which demonstrate the effectiveness of the invention.

DETAILED DESCRIPTION OF THE INVENTION

In accordance with the present invention *Lactobacillus acidophilus, Lactobacillus rhamnosus* or other lactobacillus species, such as *L. bulgaricus, L. thermophilus*, etc. bacteria are micro-encapsulated and used for oral, topical or vaginal application, for the prevention or treatment of diseases and conditions described below. The various species of lactobacilli are hereinafter collectively referred to under that name, unless a specific species is described which is then referred to by its more definite name. It was found in accordance with the present invention that micro-encapsulation of the bacteria is of great advantage in terms of therapeutic utility when compared to treatment or attempted treatment of the same conditions with lactobacilli which are not micro-encapsulated. First, the micro-encapsulation significantly increases the shelf-life of the bacteria. Even more importantly, however, after application to the human or other mammalian body, orally, topically or intra-vaginally, the encapsulating film slowly disintegrates and gradually releases the lactobacilli bacteria into its environment, namely into the lower intestines, on the skin, or in the vagina, as applicable. When the micro-encapsulated lactobacilli are used for oral administration, the micro-encapsulation provides protection to the lactobacilli bacteria against gastric juices, and allows viable lactobacilli to reach the lower intestines where they are able to have beneficial therapeutic effect.

Whereas several forms of delivery may be used to deliver the micro-encapsulated lactobacilli bacteria to its intended place of action (orally to the lower intestines, topically to the skin, or intra-vaginally) it is generally speaking necessary to have at least approximately $10^3$ viable lactobacilli bacteria in each unit dosage form, whether it be a gelatin capsule, cream, ointments, powder applied to a skin area or vaginal suppository. This means that generally speaking there is at least $10^3$ viable micro-encapsulated lactobacilli in each gram or milliliter of the pharmaceutical composition of the invention. More preferably, the concentration of the lactobacilli bacteria in the delivery vehicle or pharmaceutical composition is in the range of approximately $10^3$ to $10^{12}$ viable bacteria per gram, or per milliliter of the pharmaceutical composition, with the range of $10^5$ to $10^{12}$ being even more preferred. In this regard it is noted that $10^{12}$ bacteria per gram or per milliliter essentially represents the highest number of lactobacilli bacteria which can be given in a gram or milliliter of material. The presently most preferred concentration of lactobacilli for topical or oral application is approximately $10^6$ to $10^7$ viable micro-encapsulated bacteria per milliliter or gram of composition.

In the preferred embodiments of the invention, the bacteria are of the *Lactobacillus rhamnosus* species. Although some bacteriologists may consider *Lactobacillus rhamnosus* as a separate but related species to *Lactobacillus acidophilus*, *rhamnosus* is more properly considered a simple variant of the *acidophilus* species. As is known in the art, both *Lactobacillus acidophilus* and *Lactobacillus rhamnosus* and other lactobacilli species are "friendly" bacteria, and form a healthy intra-vaginal bacterial flora and are also part of the healthy lower intestinal flora. Both of these bacteria are known to produce certain bactericidins and hydrogen peroxide, which helps to suppress pathogenic bacteria. The advantage of *Lactobacillus rhamnosus* over the *acidophilus* variant in the present invention is in the facts that the *rhamnosus* variant is more prolific (about 8 to 10 times), and is capable of fermenting more carbohydrates (23 compared to 12 of the *acidophilus* variant) and that the *rhamnosus* variant produces $L^+$ lactic acid instead of a racemic mixture of lactic acid produced by the *acidophilus* variant. The foregoing are advantageous because the *rhamnosus* variant's ability to ferment more types of carbohydrates makes it a more sturdy, survival-prone bacteria. Production of $L^+$ lactic acid is advantageous because it is the $L^+$ enantiomer which has substantial antifungal action.

Both the *Lactobacillus acidophilus* and *Lactobacillus rhamnosus* variant bacteria used in the preferred embodiments of the present invention can be purchased from commercial sources, or can be obtained from laboratory strains. The *Lactobacillus rhamnosus* variant used in the below described preferred embodiments is obtained from the Institute Rosell Montreal, Quebec Canada. The Lactobacillus variant is micro encapsulated in accordance with the present invention, and is formulated into a pharmaceutical composition suitable for oral, topical or vaginal application. Several methods or procedures for micro encapsulating these bacteria are described below. The purpose of micro encapsulating the bacteria is to increase their shelf-life, assure that sufficient number of viable lactobacilli bacteria survive to reach the lower intestines in case of oral administration, and to provide a slow and gradual release in case of topical and intra-vaginal administration. The material or coating which encapsulates the bacteria is selected in such a manner in accordance with the present invention that the material loses its structural integrity as a film in the intestinal or vaginal environment, or upon application to the skin (primarily due to moisture) and releases the lactobacilli bacteria.

Several methods or procedures for micro-encapsulating the lactobacilli bacteria are described below.

ENCAPSULATION METHODS

Viable, lyophilized lactobacilli bacteria that have been lyophilized after the removal of the media are used for encapsulation. The bacteria can be obtained from commercial sources, or can be obtained from laboratory strains. In the currently preferred embodiments *Lactobacillus rhamnosus* bacteria are purchased from Institute Rosell Montreal, Quebec, Canada. The organisms are grown to log phase in nutrient media. Suitable media include Thayer-Martin media, Trypticase Soy, Brain-Heart Infusion Broth, or any other enriched media suitable for the cultivation of these organisms, as no particular media is critical. The only important factors are the viability and quantity of the microorganisms that are always determined by standard clinical laboratory dilution methods, such as plating the quantified dilution of bacteria on to blood agar plates or other enriched media, incubating at 37 degrees C. for 24–48 hours in a 5–10% carbon dioxide atmosphere, and then performing a colony count. The removal of the nutrient media is done by centrifugation at 14,000×g at 0°–4° C., and then washing with sterile, balanced salts and 5% glucose solution at least three times after the initial centrifugation. The bacteria are then "snap frozen" with liquid nitrogen and then lyophilized under high vacuum.

Encapsulation Method A

The freshly obtained, washed and lyophilized bacteria obtained as described above are suspended in 10 ml of 5% glucose saline solution in such volume so as to obtain a heavy suspension of bacteria which contains between one and ten billion organisms per ml, at 0–4 degrees C. All of these procedures are performed in the 0–4 degrees C. temperature range unless otherwise noted, in order to maintain viability of the lactobacilli bacteria which at room temperature lose viability. The suspension of bacteria is rapidly, but gently, stirred while 0.2–0.4 ml of sodium alginate solution (1.5% weight by volume) is added. The above mixture is then transferred into a 4 liter round bottom flask by using a nitrogen stream through a sheathed 14 gauge needle. The 4 liter round bottom flask was previously washed with a 5% albumin solution, and thereafter heated for at least 10 hours at 65 degrees C., and the needle and the tubing used in the process have also been treated this way.

Thereafter the above mixture is forced through a 30 gauge multi-beveled needle under pressure using a large syringe and nitrogen stream. Very small droplets are generated at the end of the needle which are dried by the nitrogen and air stream around the 30 gauge needle, and the droplets are collected in an aqueous solution of 1.3–2% calcium chloride where they gel. Thereafter, they are washed at least three times with 0.08–0.13% 2-(N-cyclohexyl-amino) ethanesulfonic acid (CHES) solution and 1.0–1.5% calcium chloride solution.

The gelled droplets or little spheres are further washed with at least a five fold excess of the 0.1% CHES 1.1% calcium chloride, and normal saline solution. The resultant spheres are then "snap frozen" in liquid nitrogen and then lyophilized. After these steps, the encapsulated organisms can be used in the formulations of the present invention.

Encapsulation Method B

As an improvement over Encapsulation Method A, the following further steps are performed to render the bacteria more resistant to the cationic antimicrobials. The steps are performed at 0–4 degrees C. Thus, after the washings described in Encapsulation Method n the materials are reacted with poly L-lysine (Sigma) solution (0.05% w/v) spheres for ten minutes. The spheres are then washed with normal saline buffered to pH 4.5 with lactic acid. The resultant spheres are then "snap frozen" in liquid nitrogen and then lyophilized. After these steps, the encapsulated organisms can be used in the formulations of the present invention.

Encapsulation Method C

At 0–4 degrees C., the freshly obtained, washed, lyophilized bacteria are mixed with hydroxypropylmethylcellulose to achieve a weight to weight ratio of bacteria to the hydroxypropylmethylcellulose of 10/90, although the range can vary from 1/99 to 99/1, respectively. This will effect the final mass and viability of encapsulated organisms. It should be understood that higher ratios of cellulose tend to "protect" the bacteria in the encapsulation process. The mixture of lyophilized bacteria and hydroxypropyl methylcellulose is encapsulated by "pan" coating. This is done by using a stainless steel round bottom flask which first had been "coated" with about 1% magnesium stearate, suspension in water. A combination of a freely water permeable acrylic methacrylic acid ester copolymer and a partially water permeable acrylic methacrylic acid ester copolymer, (EUDRAGIT RL198 and EUDRAGIT RS198, respectively (obtained from Rohm Parm. Ltd., Germany) is suspended at 5–10% concentration in acetone-isopropanol, 1:1, containing a 1% w/v of castor oil. The ratio of the two copolymers can vary from 1:1 to 1:10, with a preferred ratio of 1:2. The suspension is contained in the stainless steel round bottom flask. As the suspension of the copolymer kills bacteria rapidly, the process has to be performed rapidly with a high ratio of the hydroxypropylmethyl cellulose to bacteria. Thus, the mixtures of bacteria and cellulose are added to the stainless steel flask in small amounts, agitating vigorously for 3–10 minutes while the material is being dried over a nitrogen stream.

Encapsulation Method D

The freshly obtained, washed, lyophilized bacteria are added using rapid, but gentle stirring at 0–4 degrees C. to a thick suspension of polyvinylpyrrolidone (commercially available BASF, Germany) which may or may not be crosslinked, for 2 to 12 hours with a one percent (1%) solution of divinylbenzene (Biorad) in a 5% glucose balanced salts solution at a pH of 5.0 (range 4.5–8.0). The lactobacilli become encapsulated by stirring in this mixture for 1–12 hours. The material is then "snap frozen" and lyophylized.

Encapsulation Method E

The freshly obtained, washed, lyophilized bacteria are added using rapid, but gentle stirring to a suspension of polyvinylpovidone (Crospovidone™). Specifically, ten grams of lyophilized bacteria are added to a suspension of 50 gm of polyvinylpovidone (Crospovidone™) at 0–4 degrees C. The encapsulation occurs by stirring for 30–60 minutes, although longer times can be used. Moisture is then removed from the mixture with a vacuum in a desiccator, or the material is "snap frozen" and lyophylized.

Oral Administration of Micro-Encapsulated Lactobacilli

Micro-encapsulated lactobacilli (in accordance with the presently preferred embodiment micro-encapsulated *Lactobacillus rhamnosus* variant) are administered orally to persons who suffer from antibiotic induced diarrhea or other form of acute or chronic diarrhea and its resultant complications. It was discovered in accordance with the present invention that such treatment with micro-encapsulated lactobacilli significantly reduces or eliminates the symptoms of antibiotic induced diarrhea. Examples of antibiotics, the diarrhea side effects of which are significantly diminished or eliminated by the treatment in accordance with the present invention, include clindamycin, ampicillin or tetracycline. Those skilled in the art will readily understand that the antibiotics are administered to the patient as a medical necessity for treatment of an underlying infection, and that the treatment with the micro-encapsulated lactobacilli in accordance with the present invention accompanies the antibiotic treatment to eliminate or reduce its side effects. In the event, a patient suffers from infection with *Clostridium difficile*, treatment with the drug metronidazole, vancomycin or other suitable drug is also recommended in accordance with the present invention, because these drugs kill the *C. difficile* bacteria.

Many vehicles well known in the art which are normally suitable for oral delivery of drugs or pharmaceuticals can also be utilized for the oral administration of micro-encapsulated lactobacilli, in accordance with the present invention. Generally speaking the oral dose of micro-encapsulated lactobacilli for an adult patient suffering from antibiotic induced or other form of acute or chronic diarrhea is approximately $4 \times 10^3$ to $4 \times 10^{12}$ viable bacteria per day, which is preferably provided in 4 substantially equal doses per day. Even more preferably, approximately $10^5$ to $10^{12}$ viable micro-encapsulated bacteria are administered orally, approximately 4 times a day. The oral doses of the bacteria may be admixed with pharmaceutical excipients which are otherwise well known in the art, to form tablets, powders, oral liquid doses, drops, or the micro-encapsulated bacteria may be contained and administered in capsules, such as gelatin capsules. Liquid doses and drops however, should be prepared freshly, otherwise the liquid breaks down the micro-encapsulation film and adversely affects the viability of the bacteria when exposed to gastric juices. The presently preferred mode of oral administration of micro-encapsulated lactobacilli is in capsules. In this regard it is noted that a capsule such as a gelatin capsule serving as a container for micro-encapsulated lactobacilli is considered for the purposes of the present description a "pharmaceutically acceptable excipient" because it serves to deliver oral doses of the "active ingredient", namely the micro-encapsulated lactobacilli. Other pharmaceutically acceptable excipients are materials well known in the art for tablet or powder formation, such as starch, microcrystalline cellulose, buffering and flavoring agents. Still more excipients are described below in connection with the descriptions of delivery vehicles for topical (skin) and intra-vaginal application. Although this is not the presently preferred embodiment, the micro-encapsulated lactobacilli can also be combined in a formulation for oral delivery with an antibiotic or other drug which is to be administered to the patient.

Effectiveness of orally applied micro-encapsulated lactobacilli for significantly reducing or eliminating the diarrhea side effects of antibiotics is demonstrated by the following clinical test.

Clinical Test for Oral Application

For this study, five patients with a history of recurrent, antibiotic associated diarrhea were given oral encapsulated lactobacilli to prevent their antibiotic associated diarrhea. The encapsulated lactobacilli were given four times a day at the initiation of the antimicrobial therapy and were continued for three days after the antibiotic therapy was discontinued. All of these patients were given antibiotics for appropriate medical indications that were completely independent of this study. An oral consent was obtained and the potential risks and benefits of this study were explained in detail. The patients were treated with $10^6$ encapsulated lactobacilli per dose that had been prepared according to Encapsulation Method B, which involved a poly-lysine base that was safe for oral administration. The preparation was given in a gelatin capsule filled with the encapsulated micro-organisms at the above dose (approximately $10^6$ viable bacteria per capsule).

TABLE 1

Patient Profiles with Antibiotic Associated Diarrhea

| Patient Number | Sex | Age | Usual Duration of Antibiotic Associated Diarrhea by History | Antibiotic | Dose of antibiotic |
|---|---|---|---|---|---|
| 1 | F | 29 | 6–7 Days | Clindamycin | 300 mg q.i.d. |
| 2 | F | 33 | 4–5 Days | Clindamycin | 300 mg q.i.d. |
| 3 | F | 42 | 4–5 Days | Ampicillin | 500 mg q.i.d. |
| 4 | F | 45 | 3–4 Days | Ampicillin | 500 mg q.i.d. |
| 5 | M | 40 | 4–5 Days | Tetracycline | 500 mg q.i.d. |

"q. i. d." is 4 times daily

Results of Oral Therapy with the Encapsulated Lactobacilli

In all of these patients there were no problems with diarrhea or other changes in bowel habits or symptoms. In this group of patients, there were no untoward effects of any kind from the therapy. This successful therapeutic result in this population could only be attributed to the oral therapy with the encapsulated lactobacilli. Oral administration of micro-encapsulated lactobacilli in accordance with the present invention is suitable for treatment not only for humans, but other mammals as well.

Clinical Test for Topical Application of Micro-encapsulated Lactobacilli to Prevent Skin Infections For this study, five patients with a history of recurrent skin infections were given topical encapsulated lactobacilli to prevent skin infections. These patients were selected because they all had conditions that predisposed these individuals to chronic, recurrent skin infections. In all of these patients an oral consent was obtained and the potential risks and benefits of this study were explained in detail. The topical micro-encapsulated lactobacilli were applied to the affected skin area three times a day for six months. Each administration of the lactobacilli was made with $10^6$ encapsulated organisms which had been prepared according to Encapsulation Method D. The encapsulated organisms were mixed with talc to give a homogeneous powder to apply to the application site. The concentration of viable bacteria in the formulation which was applied to the skin was approximately $10^6$ bacteria per gram, and depending on the area treated approximately ½ to 1 gram was used in application.

TABLE 2

The Topical Use of Encapsulated Lactobacilli to Retard Skin Infections

| Patient Number | Age | Pre-Disposing Factor(s) | Sex and Race | Site of Infection | Fungal Organisms Isolated |
|---|---|---|---|---|---|
| 1 | 31 | Anabolic Steroid Abuse | White | Groin | T.r., T.v. |
| 2 | 33 | Anabolic Steroid Abuse | Black | Groin | T.r., T.v. |

TABLE 2-continued

The Topical Use of Encapsulated Lactobacilli to Retard Skin Infections

| Patient Number | Age | Pre-Disposing Factor(s) | Sex and Race | Site of Infection | Fungal Organisms Isolated |
|---|---|---|---|---|---|
| 3 | 27 | Anabolic Steroid Abuse | White | Groin | T.r., T.m. |
| 4 | 59 | Morbid Obesity Diabetes Mellitus | White Female | Abdominal pannus | C.a. |
| 5 | 39 | Diabetes Mellitus | White Female | Abdominal pannus | C.a. |

C.a. is *Candida albicans*, T.r. is *Trichophyton rubrum*, T.v. is *Trichophyton verrucosum*, and T.m. is *Trichophyton mentagrophytes*.

Results of Topical Application of Encapsulated Lactobacilli

In this study with patients using the topically applied, micro-encapsulated lactobacilli three times a day, there were no yeast infections observed in any of the patient for the entire study period. Also, there were no untoward reactions of any kind in any of these patients. It should be understood in this regard, that topical use of micro-encapsulated lactobacilli in accordance with the present invention is not limited to the skin areas which were treated in the 5 patients in the above-described test. Rather the pharmaceutical composition of the present invention is suitable for treating or preventing skin infections in substantially any area of the skin in humans, and in mammals.

Clinical Test for Intra-Vaginal Application of Micro-encapsulated Lactobacilli to Decrease the Risk of Infections It is the consensus of current medical and scientific thinking and is reflected in a great volume of scientific literature that a "normal" vaginal flora must contain appropriate lactobacilli as the major species. Moreover, it is desirable that the lactobacilli of the flora should produce both hydrogen peroxide and microbiocidins. In order to demonstrate the utility of the topical vaginal application of micro-encapsulated lactobacilli to prevent vaginal infections, five patients with a history of more than six, recurrent vaginal infections per year and with predisposing factors to vaginal infections were selected for the topical, vaginal therapy with micro-encapsulated lactobacilli. In all of these patients an oral consent was obtained and the potential risks and benefits of this study were explained in detail. The topical, micro-encapsulated lactobacilli were applied once a day, nightly at bedtime for six months. For ethical reasons this study did not have a "placebo arm" and the patients' previous history was used as the "control". All of these patients in this test were treated with clotrimazole (trade name Mycelex-G 500, one 500 mg suppository) at bedtime for one week prior to the initiation of this study. This therapy was necessary because all of these patients had symptomatic infections with the fungal organisms identified below in Table 3, which had to be eradicated prior to the initiation of this study. The patients were treated with $10^6$ encapsulated lactobacilli per dose that had been prepared according to Encapsulation Method C, which involved a cellulose base. The product of Encapsulation Method C can be formed in a mold into a solid or semi-solid suppository-shaped object which allows for the easy insertion into the vagina. Optionally, additional cellulose or lactose or other conventional ingredients can be added to the suppository.

In this regard it is noted that, generally speaking, for topical application and for intra-vaginal use a great variety of delivery vehicles (formulations) otherwise known in the art can be used. For example, the micro-encapsulated lactobacilli can be mixed with corn-starch, talcum or other suitable powder material. Creams, foams and ointments and conventional suppositories can be prepared, where, in addition to the active ingredient micro-encapsulated lactobacilli, fillers such as micro-crystalline cellulose, hydroxypropylmethyl cellulose, magnesium stearate, silicon dioxide, and lactose may be used. Still further optional components or ingredients which may be included in the suppository, or cream, foam, ointment, powder or other formulation of the present invention are fragrances, menthol, eucalyptus oil, methyl salicylate or related salicylates as topical cooling agents; hydrocortizone or related antiinflammatory steroids (1 to 500 mg per suppository) as anti-inflammatory agents; EDTA as a wetting agent and mild antimicrobial; propylene glycol or other pharmaceutically acceptable glycols, methyl paraben or related paraben derivatives as wetting agents and for "texture"; para diisobutylphenoxy polyethoxyethanol, nonoxynol-9 or dodoecaethylene glycol monolaurate as spermicidal and mild antimicrobial agents; tritions and menfegol as spermicidal, mild antimicrobial and wetting agents.

TABLE 3

Intra-Vaginal Use of Encapsulated Lactobacilli to Retard Vaginal Infections

| Patent Number and Age | Pre-Disposing Factor(s) | Number of Vaginal Infections Per Year Prior to Therapy | Dominate Micro-Organism(s) Isolated Prior to Therapy | Dominate Micro-Organism(s) Isolated After Therapy |
|---|---|---|---|---|
| 1 33 yrs. | Diabetes, obesity | 9 | C.a. | L.a., L.r. |
| 2 45 yrs. | Diabetes obesity | 10 | C.a. | L.a., L.r. |
| 3 29 yrs. | Obesity, cytotoxic therapy | 8 | C.g. | L.a., L.r. |
| 4 41 yrs. | Diabetes, obesity, cytotoxic therapy, auto-immune disease | 11 | C.a., C.p. | L.a., L.r. |
| 5 37 yrs. | Diabetes, obesity, cytotoxic therapy | 10 | C.t. | L.a., L.r. |

C.a., is *Candida albicans*, C.g. is *Candida glabrata*, C.t. is *Candida tropicalis*, C.p. is *Candida parapsilosis*, L.a. is *Lactobacillus acidophilus*, and L.r. is *Lactobacillus rhamnosus*.

Results of Vaginal Application of Encapsulated Lactobacilli

In this study with patients using the topically, intra-vaginally applied, micro-encapsulated lactobacilli at bedtime, there were no yeast infections observed in any patient for the entire study period. Also, there were no untoward reactions of any kind in any of these patients, and as it can be seen after treatment the predominant organisms in the vaginal flora were the beneficial *Lactobacillus acidophilus* or *Lactobacillus rhamnosus* bacteria.

What is claimed is:

1. A pharmaceutical composition adapted for intra-vaginal delivery to a human patient, comprising in a unit dose thereof at least approximately $10^3$ viable lactobacilli bacteria, said lactobacilli bacteria being micro-encapsulated whereby the lactobacilli bacteria stay viable during storage of the composition, the substance providing the encapsulating coating for the lactobacilli bacteria being such that it releases lactobacilli bacteria upon prolonged exposure to moisture.

2. The pharmaceutical composition of claim 1 which is a vaginal suppository.

3. The pharmaceutical composition of claim 2 wherein each suppository comprises at least approximately $10^5$ viable lactobacilli bacteria of the *Lactobacillus acidophilus* species or of its *Lactobacillus rhamnosus* variant.

4. A method of treating or preventing yeast infection in a female mammal, including a female human, by intra-vaginally delivering to said female a pharmaceutical composition comprising in a unit dose thereof at least approximately $10^3$ viable lactobacilli lactobacilli bacteria, said lactobacilli bacteria being micro-encapsulated whereby the lactobacilli bacteria stay viable during storage of the composition, the substance providing the encapsulating coating for the lactobacilli bacteria being such that it releases lactobacilli bacteria upon prolonged exposure to moisture in the vagina.

5. The method of claim 4 wherein the pharmaceutical composition is a vaginal suppository, comprising at least approximately $10^5$ viable micro-encapsulated lactobacilli bacteria of the *Lactobacillus acidophilus* species or of its *Lactobacillus rhamnosus* variant.

* * * * *